United States Patent [19]
Daniel

[11] 4,234,907
[45] Nov. 18, 1980

[54] LIGHT EMITTING FABRIC

[76] Inventor: Maurice Daniel, 550 Jaycox Rd., Avon Lake, Ohio 44012

[21] Appl. No.: 7,592

[22] Filed: Jan. 29, 1979

[51] Int. Cl.³ .............................................. F21V 7/04
[52] U.S. Cl. ..................................... 362/32; 362/103; 362/108; 362/806; 362/812
[58] Field of Search ................. 362/32, 806, 812, 103, 362/108

[56] References Cited
U.S. PATENT DOCUMENTS
3,760,179  9/1973  Addington .............................. 362/32

*Primary Examiner*—Stephen J. Lechert, Jr.
*Attorney, Agent, or Firm*—Sixbey, Friedman & Leedom

[57] ABSTRACT

A light emitting fabric (10) in which optical fibers (12, 28, 46, 48) are part of the weave, replacing some of the threaded fibers (27), whereby the fabric is uniformly illuminated and, accordingly, decorated. The individual optical fibers are gathered into a bundle (15) at one end of the fabric and illuminated by a light source (17). Light traveling through the fibers is emitted in small amounts throughout the lengths thereof through small scratches (14) that pierce the outer coating. Uniformity and intensity of light are enhanced by providing a reflective coating (13) on the non-illuminated ends of the optical fibers. This fabric is usable in clothing; such as costumes, high visibility safety clothing, suntan suits (21); rugs, draperies, theater curtains, architectural panels (23), fiberglass boat hulls, and the like.

35 Claims, 14 Drawing Figures

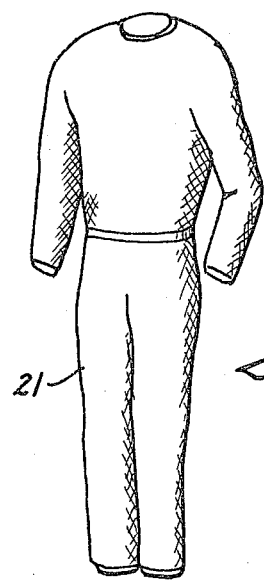
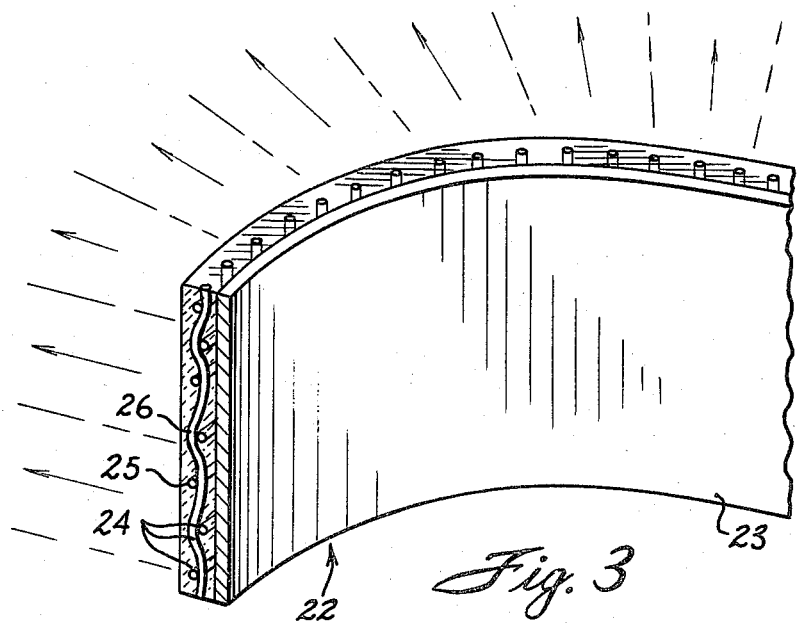

LIGHT EMITTING FABRIC

BACKGROUND OF THE INVENTION

This invention is directed to an illuminated fabric, and more particularly, to a fabric into which optical fibers are actually woven.

The best known prior illumination of fabric is found in the U.S. Pat. No. 3,549,878 issued to Richard E. Bailey on Dec. 22, 1970. Light is provided by a plurality of bulbs which are wired to a battery concealed on the person. In the fiber optic art, U.S. Pat. Nos. 3,718,814 issued Feb. 27, 1973 to Van Slyke; 3,781,537 issued Dec. 25, 1973 to Ramsey; and 3,526,880 issued Sept. 1, 1970 to Filippazzi teach the treatment of optical filaments to permit lateral escape of light therefrom.

The instant invention is a novel incorporation of the fiber optic filaments as a replacement for the conventional fibers of a fabric, such as warp and woof, or both, thereof. Whereas the fibers of the prior art are made into panels or are inputted to photocells, the fibers of this invention are utilized as a multiple source of decorative illumination for a variety of items. Further, this invention provides a uniformity of illumination not anticipated by the prior fiber optic references known by this inventor.

SUMMARY OF THE INVENTION

It is, therefore, an object of this invention to provide a fabric utilizing fiber optic illumination wherein the fiber optic elements are threads of the fabric. Another object of this invention is to provide a means for illuminating an item of clothing by the use of fiber optics. It is an object to provide uniform illumination by discrete spacing and notching of the side of the optical fiber. Still another object of this invention is to provide a pleasing illumination means for a floor or a wall covering. Further, it is an object of this invention to provide a means for intensifying the light emitted laterally from the optical fibers. Included in the objects of this invention is to increase the number of choices available for use of an interior decorator and an architect. Another object is to provide an architectural panel wherewith exterior sections can be illuminated and whereby an entrance to a building can be provided with heat. Still other objects include the provision of a suit of clothing of high visibility as would be useful to a person directing automobile traffic, or to a performer who chose clothing of glowing color for his act, especially in parades. Also, it is an object to provide a suntan suit or a warm suit.

The fiber optics used for illumination, heat or suntan purposes are woven to become a part of the fabric in which they are utilized. A color means in the light source means provides for any color choice for the fabric, including changing colors in response to desire; rotating color wheels, or any other variable input means can be used.

In accordance with these and other objects which will become apparent hereinafter, the instant invention will now be described with reference to the accompanying drawings in which:

FIG. 2 shows the fabric of this invention prepared in the form of a suit of clothing;

FIG. 3 shows the fiber optic illumination means as a part of an architectural panel;

DESCRIPTION OF A PREFERRED EMBODIMENT

Figure 1:
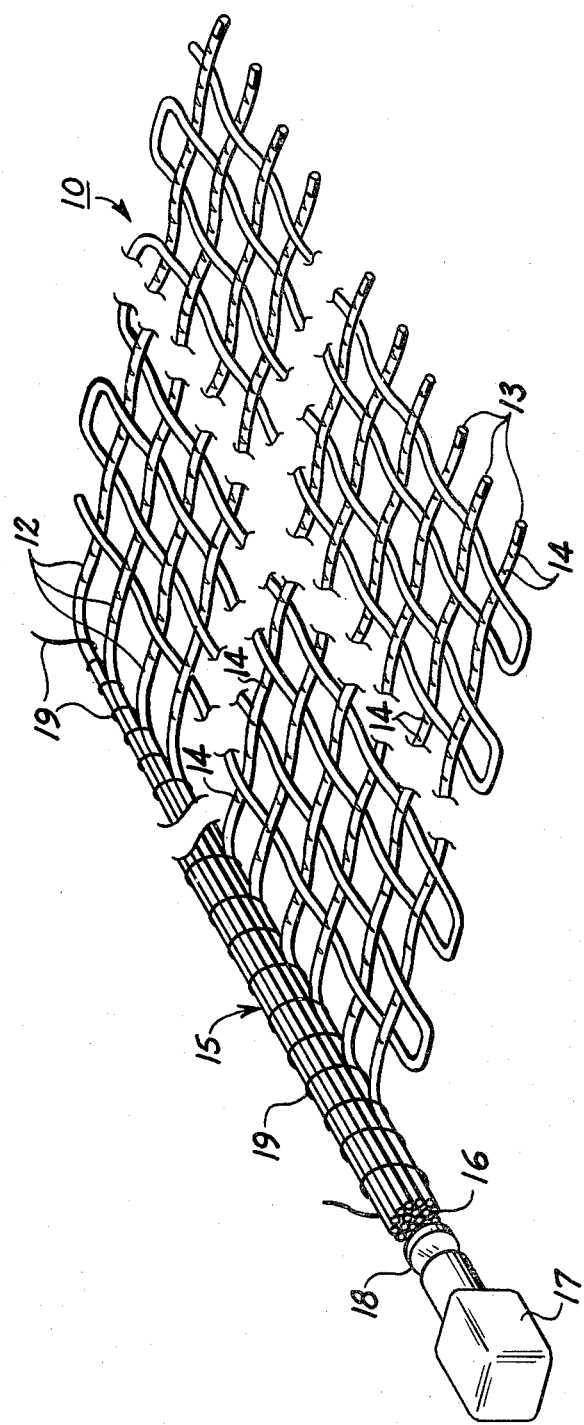
FIG. 1 shows the woven fiber optic cloth in enlargement.

Turning now to the drawings wherein like reference characters designate the like or corresponding parts throughout the various views, and referring particularly to FIG. 1, there is shown the fabric 10 in which the cloth threads 11 are shown with the fiber optic filaments 12 being woven therewith. By definition, the woof threads are the threads usually carried by the shuttle in weaving, whereas the warp threads extend lengthwise in the loom, crossed by the woof.

In FIG. 1, the woof threads are made of conventional fibers, such as cotton, nylon, wool, and the like, and the warp threads are made of single optical fibers. At the ends of the optical fibers 12 are mirrors or reflecting surfaces 13 to reflect back into the fiber the residual light remaining after the passage of the light through the length of the fiber. A plurality of notches 14 are spaced increasingly closer to each other as the distance from the light source 15 increases. In other words, the closer to the light source, the more light is in the fiber and, accordingly, available to escape through the notch 14. To compensate for the light fall-off downstream from the source, the notches 14 are placed closer together to permit an even amount of escaped light across the fabric. The fibers are formed into a bundle 15 in order to make the end 16 of the optical fibers nearest the light source dimensionally correct to receive the light from light source 17 as shown in FIG. 1. The light source 17 is a conventional light producing means suited to the amount and cross-sectional area needed for individual applications. Also shown in FIG. 1 is a color producing means 18 which can be a single desired color, or in other cases, a rotatable variegated multiple color means for producing changing effects.

The bundle 15 of optical fibers leading from the source 17 can be secured into a unitary element either by lacing 19 or by any other conventional means of making fiber optics into a bundle.

As already set forth, this invention is directed to a product which has a wide variety of applications in several areas of endeavor. It serves as a basic new industrial material. In it is the capability of increasing the utility and design of many existing products. This fabric can be made to give off white or colored light. Light emitting cloth could be used in clothing as a new and attention getting novelty. A wide usage would be in theater curtains whereby the several required light sources would be located at the top of the curtain and a sufficient number of light emitting sources would be supplied to illuminate the curtain brilliantly. Light emitting household draperies would take on a glow to add an esthetic accent to a room decor. Also accomplished is uniform lighting for uses in photography, television, and in other areas where present illumination means are less than suitable. These products are made possible by the weaving of optical fibers 12 and conventional fibers 11 into cloth 10. All the optical fibers would be gathered into a bundle 15 at one end of a sheet of cloth and stuck into one end of a light source 17 that would be arranged so as to send light through the fibers 12.

Normally, the light passing through an optical fiber passes out the end thereof after a certain amount of loss from the medium. Cloth woven of such fibers would not light up except at the ends of the optical fibers. In order to cause light to be emitted along the lengths of the optical fibers, it is proposed to scratch or otherwise cause mechanical, chemical, or other deformation of the optical fibers at discrete locations along their lengths. If these scratches or deformations are small enough, only a small portion of the light passing therethrough is emitted through each scratch. When all of the optical fibers are scratched at decreasingly spaced intervals, in some artfully selected proportion as their distance from the light source increases, a uniform emission of light is seen by the human eye to be emitted along their entire lengths, when viewed from a distance. The light being emitted through these scratches along the lengths of optical fibers can be increased by coating the ends of the fibers, that are remote from the light source, with a reflective coating. This reflective coating returns the light, that would normally be lost out the fiber ends, back along the fiber lengths where much of it is emitted through the scratches to provide additional illumination.

Various coatings may be applied to the optical fibers either before or after the fabric is woven. Such coatings as are useful in dyeing, in aiding the weaving process, in strengthening the fibers, in increasing the wear resistance of the fibers, or are useful in other ways, may be applied to the optical fibers. A plurality of such coatings may be applied to the optical fibers that are incorporated into a light emitting fabric. However, any coating that is applied immediately after the optical fibers are scratched must be applied with an awareness of the light emission problems that coatings contribute. Due concern must be given for the exact geometry of the scratched or altered optical fibers along with the relative indices of refraction of such coating and of the optical fibers. This is in order that the coating does not alter the light emissivity of the scratched optical fibers in some undesirable way.

The usefulness of some composite materials, such as the fiberglass used in some boat hulls, automobile bodies, furniture, sports and industrial equipment, and the like, can be enhanced in novel ways by the use of light emitting fabrics. A woven fabric of optical fibers and conventional glass or other fibers can serve as a matrix material in the fabrication of fiberglass products with little or no loss of strength nor utility. In particular, light emitting fiberglass panels can be made of an optical and glass fiber matrix which has been impregnated with an epoxy resin and connected to a suitable light source through a length of fiber optic light pipe with suitable couplings. Such panels can be designed to serve as light emitting wall or ceiling panels and thereby serve as substitutes for conventional lighting fixtures. The capability of fiberglass to be formed into unusual shapes and exotic curves is not encumbered by the addition of an optical fiber matrix weave. Thus, light emitting fabrics used as a matrix material in some composite materials makes possible the manufacture of products having enhanced decorative and safety features.

In general, the optical fibers used in the manufacture of light emitting fabrics must have considerable mechanical flexibility in order to withstand the bending that fibers normally experience in being woven into cloth. Depending upon the specific application, the woven optical fibers should be chosen to withstand: folding without breaking the individual fibers; the solubility of water and common household solvents; and temperature extremes normally encountered by fabrics. Light emitting fabrics that must withstand washing machine wear as well as excessive flexing of the fibers must be manufactured from very flexible fiber optics that are water proof and able to resist ordinary soaps, detergents, and the temperatures commonly encountered in washing machines and dryers. Optical fibers that are woven into rugs, clothing, blankets, and other products that must withstand considerable abrasion must have special precautions taken for wear protection. The optical fibers may be coated with thick tough abrasion-resistant coatings, may be made of special abrasion resistant optical fibers, or the optical fibers may be woven only in the deeper levels of a thick fabric where abrasion is not usually encountered.

In the simplest version of this invention, single optical fibers are woven into a fabric in which conventional threads are perpendicular thereto. Many variations are possible. The single optical fibers may be replaced by small bundles of optical fibers for greater over-all strength. The cloth may be woven of threads containing mixtures of fiber optics and conventional threads in both directions or just one direction of the weave. It is a matter of the requirements of the desired end product how the distribution of optical and conventional fibers is determined. In some cases, the entire fabric can be woven of fiber optics.

Some wallpapers are made up of a sheet of cloth as the base material upon which various coatings of ink are applied. Replacement of the cloth-backed wall coverings with light emitting fabrics as described above would introduce room lighting decorative wall coverings of infinite variety. The installation of the light sources and the bundled fiber optics would, of course, require concealment thereof.

Scratched fiber optics that are woven into cloth and connected to a portable or other light source in the manner described above, can be applied to almost any item that is normally made of cloth.

Clothing is the most obvious example of a cloth item to which this invention can be applied. However, clothing applications are limited by the requirement of having to carry some sort of light source and batteries to supply the light to the light emitting fabrics. Clothing made from light emitting fabrics, therefore, have their greatest application as fad items and as safety clothing. In particular, such clothing is useful where the wearer wishes to be seen, such as in the case of a cyclist riding on the highways at night, or as in the case of a policeman or city worker who must stand on the highways during times of street traffic.

In addition to the aforesaid non-uniform notching of the optical fibers to achieve a more uniform light emission, a staggered pattern of scratching the optical fibers in different places along their lengths can be used. For example, all the optical fibers can be considered to be divided into three sets; A, B, and C. The A set could be scratched along the first third of their lengths beginning at the point of entry into the woven fabric. The B set could be scratched along the middle third of their lengths while the C set could be scratched in their third which is furthest from the light source. Each optical fiber stretches from one end of the fabric to the other with only a portion thereof emitting light while providing strength to the fabric throughout its entire length. Since some light is lost within most optical fibers due to internal absorption by the glass or plastic they are made of, a greater amount of overlapping of scratched portions may be arranged at distances further from the light source. With such flexibility of choice of placement of the scratches, it is possible to accomplish uniform light distribution all across the fabric, and it is also possible to select a decorative pattern of unevenly distributed light as desired. Additionally, the depths of the notches, scratches, or other disturbances of the coating of the optical fibers can be varied to produce desired light effects.

Optical fibers are usually designed to longitudinally transmit all wavelengths of visible light through a transparent filament that is coated by a second transparent material having a relatively lower index of refraction than the core material. However, when optical fibers are incorporated into light emitting fabrics, it is often desirable to have colored light patterns across the fabrics. One method of causing light emitting fabrics to give off colored light is to send colored light into the optical fibers by using colored light bulbs or other sources of colored light. Also, color can be added by placing a colored light filter, prism, or the like between the source of light and the point where the light enters the optical fibers. Such colored light sources can be made to vary in color and intensity by the use of motor driven color wheel filters, electronic control over the light source, and the like. Optical fibers with cores made of colored glass, or colored plastic, or the like, may be used in place of completely transparent materials to give the light emitting fabric a colored light pattern when white light is given off by the light source. The scratched optical fibers may be coated with a pattern of transparent colored plastic or like materials to create a pattern of colored light to be emitted by the light emitting fabric. Among the many patterns possible are: alphabetic characters, symbols, logos, abstract and decorative designs for items such as signs, advertisements, and lightable labels.

Ultraviolet and infrared sources can be utilized by a fiber optic in which the core is transparent to the wavelengths of such ultraviolet or infrared emissions and have an index of refraction higher than that of the coating material. Ultraviolet transmitting fabrics could be used to illuminate clothing, signs, posters, or other articles containing fluorescent dyes or inks. Ultraviolet emitting fabrics can provide uniform ultraviolet illumination for medicinal uses, ultraviolet photography, examination of documents, biological studies or any other desired application.

Turning again to the drawings, FIG. 2 illustrates an application of ultraviolet emitting fabric in the form of a suit of clothing made up of ultraviolet emitting fabric to provide a vastly improved way of obtaining a suntan. In this application, the ultraviolet transmitting optical fibers are woven into a one piece jumpsuit 21 or other one piece garment that completely covers the body. The scratches on the fibers are made only on the inside surface so that the ultraviolet light is radiated towards the skin of its user. A portable or stationary source of ultraviolet light is then connected to the garment through its fiber optics light pipe and couplings. A filter means is placed in the light pipe to prevent heat from traveling into the optical fibers and to prevent most electromagnetic radiation, except that in the 290–230 nm wavelength range needed for producing suntans, from entering the fiber optics. A timer controls the dosage of radiation the wearer is subjected to. Uniformity of tan is thereby accomplished as well as tanning under arms and on all sides at once. The timer control is more effective than that of a sunlamp since the suntan suit illuminates each square inch of body surface equally despite the folds in the garment. With the heat filter of the suntan suit, the user does not receive excessive heat—he tans in a comfortable environment. The portable radiation source permits the user to move about while receiving a suntan, so that he is not limited to a long stay in the sun or under a sun lamp.

Infrared emitting fabric is woven from infrared transmitting optical fibers and a suitable support weave made of fireproof, high melting point fibers, such as glass fibers. A support weave fiber of material transparent to infrared wavelengths would be most useful in increasing the emission of heat from the fabric. The source could be an infrared lamp, a laser, or the like. Such a fabric remains relatively cool when the radiation is passing therethrough. Most of the infrared radiation would pass through the air to strike nearby objects into which it would be absorbed according to the nature of the surface of the object and heat that surface accordingly. Heating of outdoor objects could be economically accomplished by such an infrared emitting panel. A bus stop or train station having open sides would readily benefit from this device. In a shelter, where infrared lamps are placed, the only person benefitting is the person directly under the lamp. With a panel of the present invention, the heatable area is greatly increased to accommodate a much larger group of people. The uniformity of heat available from such a panel gives more comfort to more people than an array of lamps emitting the same amount of heat energy.

In the example of a fabric which emits infrared radiation, alternate heating means are afforded thereby. Such fabrics could be made into rugs, wallpapers, ceiling tiles, and into baseboard heaters. Such heat is quieter and more even than any conventional form of heating. Infrared emitting fabrics can be used in draperies, curtains, furniture, blankets, and in other indoor furnishings to heat specific areas of a room. The fabric is usable in cold weather clothing, such as a sweat suit, or in infrared therapeutic devices. An infrared emitting ribbon warms items such as baby bottles or any desired travel food. The fabric may be used to heat the top surface of a mattress, and the fabric for automobile seats. Some industrial processes can be better served by this fabric. Large sections of infrared emitting fabric could be used to protect orchards from frost damage. The infrared panels can be used to heat entry ways and unenclosed waiting areas. Outdoor animal shelters on farms would be well served by this fabric. Wherever controlled heating is needed, this fabric is capable of being adapted for use.

Referring now to FIG. 3, a panel referred to generally as numeral 22 is constructed for architectural uses. The backing support of the panel 23 can be made of steel, wood or any other material desired therefor. Secured to the backing 23 is a fiber optic fabric 24 made up of woven fiber optics 25 and/or 26, which delivers light from the notched woven optical fibers. In one application, the light emitting fabric is set in a coating such as glass on a backing such as steel. The glass coating used to fuse the optical fabric onto the steel base creates an enamel surface capable of emitting light. Large panels thereof would be used to cover larger surfaces of large buildings. After coating the steel panels with a thin layer of glass enamel, a sheet of light emitting fabric is placed over the enamel surface along with additional powdered glass if needed and the panel is fired again in a kiln hot enough to fuse the optical fibers into the enamel surface without melting the optical fibers. The edge of the light emitting fabric having the optical fiber tails is bent around one edge of the steel panel before the final firing and gathered into a many stranded fiber optic bundle after such final firing. Once installed on the sides of a building, these light emitting enamel coated steel panels are connected in known manner to a suitable light source. Buildings having such panels are made to light up in continuously changing patterns of colored light by using an automated system of rotating colored light filters between the light sources and the fiber optics of the bundled fiber optics of the fabric. The same structure can be applied to bathroom fixtures, glass enamel coated brick or tiles, or in most other applications where glass enamel coatings are presently used.

A light emitting fully transparent window glass can be manufactured by sandwiching a special fiber optics cloth between two thin sheets of molten glass and fusing the combination together into a single sheet of glass. Threads in one direction of the weave would be made up of the same type of glass as the molten glass used to impregnate and surround the light emitting fabric so that these threads will dissolve into the molten flass and serve only to hold the optical fibers in place during fabrication. The optical fibers have a relatively higher melting point than the surrounding materials to prevent them from being dissolved. The index of refraction of the glass used for the core material is equal to or greater than the index of refraction for the glass used as the coating material in the optical fibers in order to allow light to escape from the scratches in the optical fibers. Tails of optical fibers are gathered into a bundle along one edge of the glass sheet, tied together and coated with suitable plastic, trimmed to length, and fitted with coupling means that permit the fiber optics to be attached to a suitable light source.

Glass sheets made as discussed in the above paragraph are usable for room lighting, window display glass, and as a base material for signs and other advertising displays. The optical fibers could be notched to emit light from either or both surfaces of the glass.

For any of the applications of this fabric disclosed in this application, it may be desirable to provide a plurality of layers of light emitting fabric. The fiber optic light pipes that emerge from one corner of each layer of cloth may then be attached to separate light sources, or they may obtain their light from a single source. In the latter case, the combined layers of cloth can be made to give off a greater intensity of light per unit of square area than the single layer. The light may also be made more uniform across the surface by layering, especially if light enters from differently located edges of each layer of the cloth. Each layer can be made to emit a different color of light and each can have a different pattern of scratches. The light sources may have individual movable prisms or colored filters so that the individual layers emit a variety of light pattern changes.

Figure 13:
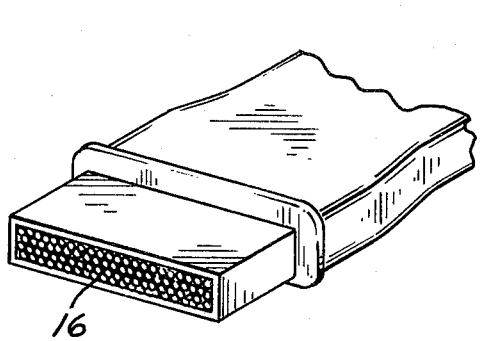
FIG. 13 shows a rectangularly configured connecting means for the fiber optic bundle.
Figure 14:
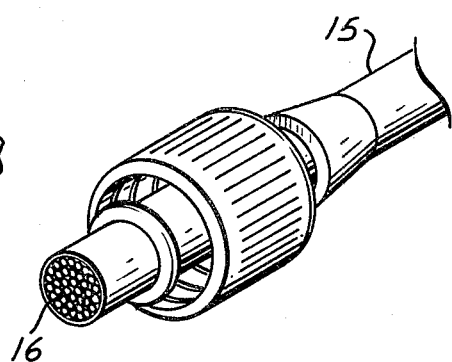
FIG. 14 shows a circular connecting means for the bundle.

The optical fibers that emerge along one or more edges of a light emitting fabric are gathered into a bundle and extended to one or more corners of the fabric where they are made into a many fibered optical light pipe with a suitable protective coating. This length of light pipe ends at some suitable distance from the corner of the cloth and is usually trimmed to a desired length. The trimmed end is polished to allow the entrance of light from the light source into the light pipe. The end of the light pipe also has a coupling or other suitable fitting attached thereto in order to readily be connected to the light source. A circular fitting is shown in FIG. 14. However, the fitting need not be circular, but often it is desired that the fitting be rectangular as shown in FIG. 13. Also, an oval, and the like, shaped fitting will serve. The flat, rectangular fitting of FIG. 13 enables the light pipe to be as inconspicuous as possible. In some designs, elimination of the light pipe would place the coupling directly in contact with the bundle as it is first formed along the edge of the fabric.

Figure 4:
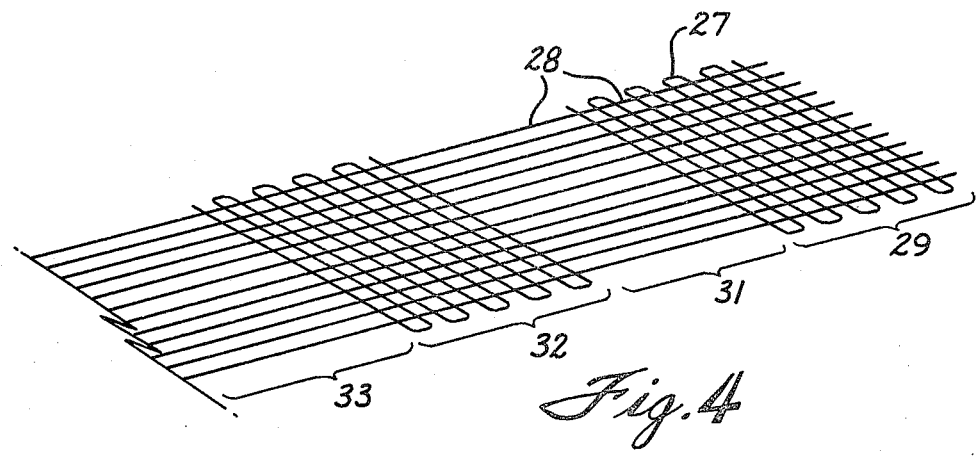
FIG. 4 shows a woven continuous strip of optical cloth.
Figure 5:
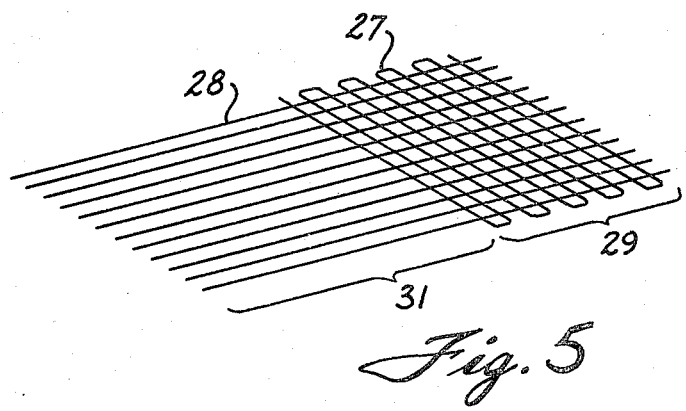
FIG. 5 shows a section of the cloth of FIG. 4 cut to be in usable form.
Figure 6:
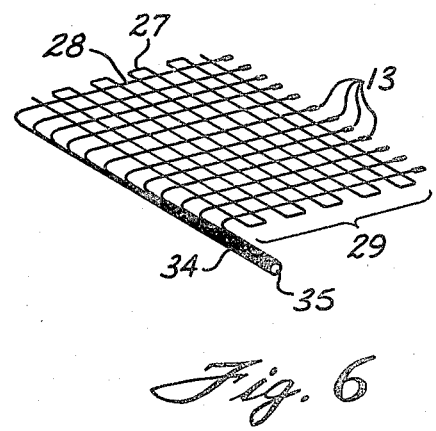
FIG. 6 shows the section shown in FIG. 5 with the unwoven ends of the optical fibers formed into a bundle in order to receive light from a source.

Turning now to FIG. 4, an example of a light emitting loomed cloth is shown. Light emitting fabrics are woven on conventional industrial looms in which optical fibers are used in place of some or all of the conventional threads. One method of weaving a light emitting fabric is to use conventional threads 27 for the woof portion of the fabric, and to use optical fibers 28 for the warp portion as shown in FIG. 4. After the loom is set up and turned on, a short length of cloth is woven with the shuttle operating as normal. When the desired size of woven fabric 29 is woven, the shuttle is turned off and a length of the fiber optics is moved through the loom without any weaving therethrough as shown at 31 in FIG. 4. When the length of the fiber optics is sufficient to form a light pipe bundle of desired length, the shuttle is again turned on and another piece of fabric 32 is woven with the fiber optic tails 33 extending therefrom. The woven fabric is cut into individual pieces as shown in FIG. 5 wherein the woven section 29 is shown with the fiber optic tails 31. As shown in FIG. 6, the fiber optic tails 31 are formed into a light pipe 34 with its end 35 available for connection to a light source.

Figure 7:
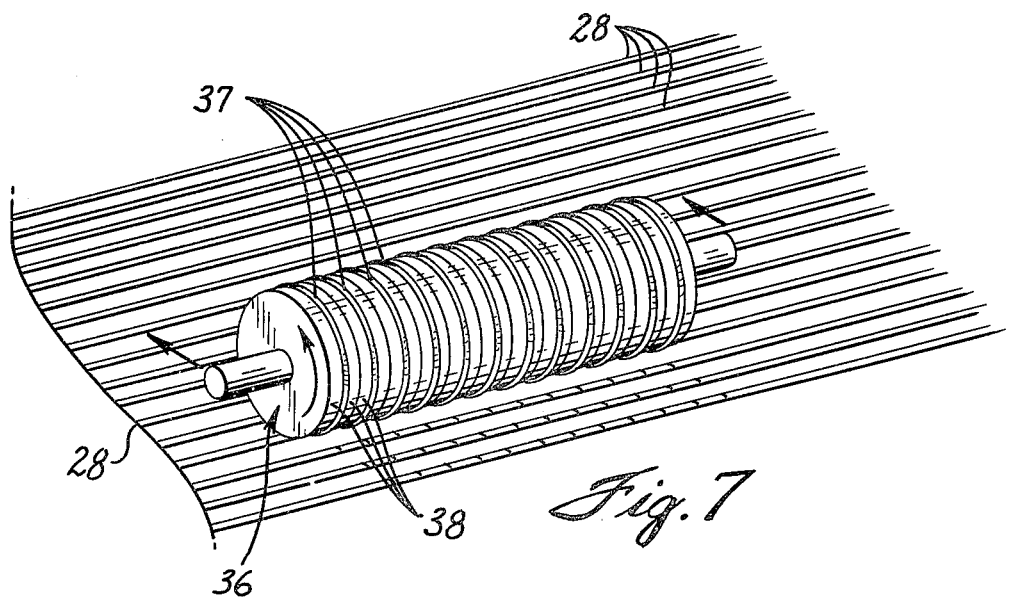
FIG. 7 shows a means for notching the fibers.
Figure 8:
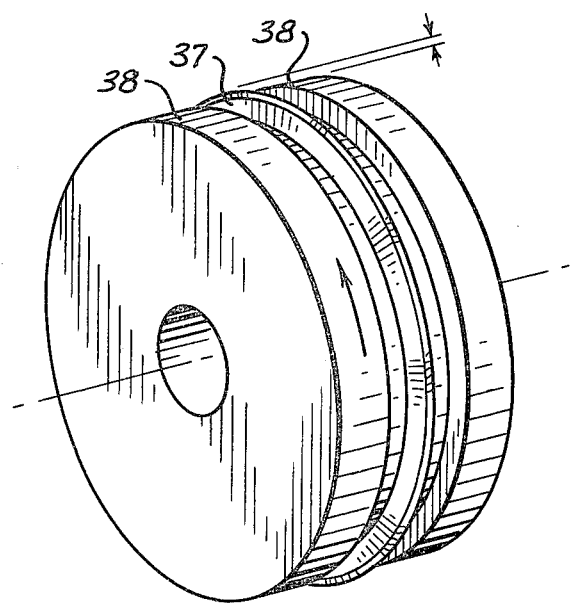
FIG. 8 shows a detail of the fiber optic notching means of FIG. 7.

Referring now to FIG. 7, before the optical fibers pass into the loom's weaving mechanism, the fibers are scratched or notched by cutting means such as cutter 36. Cutter 36 is rolled over the optical fibers to cut notches therein. Cutter 36 is made up of a plurality of shielded blades 37 which are spaced by shields 38 as seen more clearly in enlarged detail of the cutter and shield in FIG. 8. The blades 37 rotate at a high speed while the shields 38 simply make contact with and roll across the fibers. The blades extend beyond the shields by only slightly more than the thickness of the coating that covers a single strand of optical fiber. This cutter 36 requires that the fabric remains static while it is being scratched. This has the advantage that the shield wheels 38 can be made with different widths across the width of the fabric so that any desired spacing of the scratches can be obtained. The depth of the scratches is varied by using differently diametered cutting blades 37.

Figure 9:
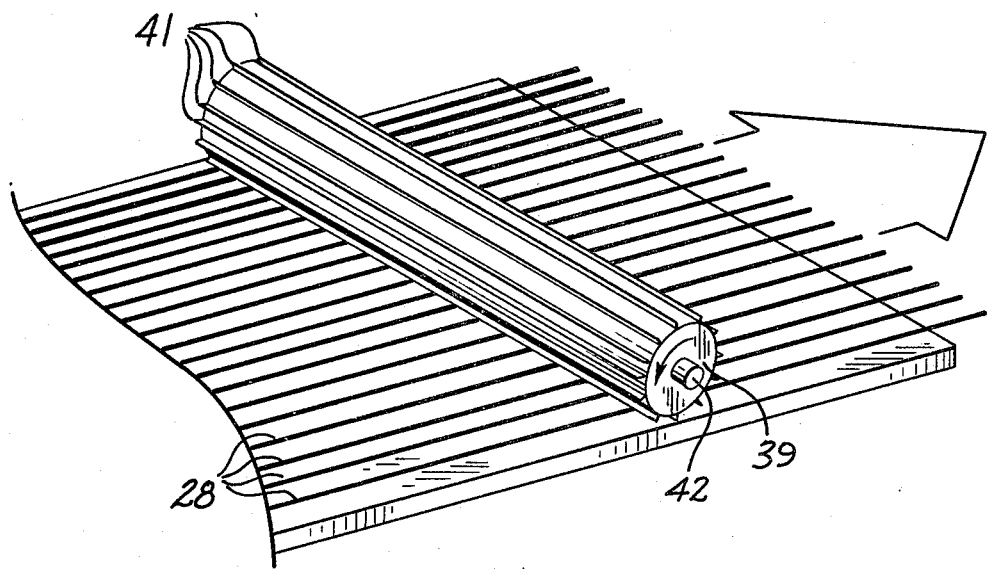
FIG. 9 shows an alternate means of notching the optical fibers.
Figure 10:
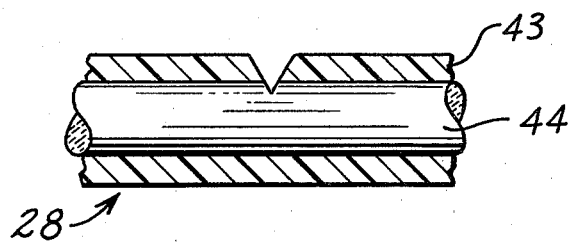
FIG. 10 shows a detail of the notch in the optical fiber.

In FIG. 9 is shown an alternate means for cutting the notches in the optical fibers. Roller 39 is made up of a plurality of cutting edges 41 and the pivot 42 of roller 39 is mounted in bearings 42 and such bearings are secured to the loom so that roller 39 rotates and does not move along the fibers. With the fibers 28 moving into the loom weaving areas, the roller 39 rotates to mark the notches on the moving fibers enabling the absence of slippage of the knife edges with respect to the fibers. As illustrated in FIG. 10, the cutting edges, or blades, extend beyond the surface of the roller for a distance large enough to scratch or notch the fiber coatings 43 to or into the fiber core 44 without cutting all the way through the fibers. The cutting blades are in contact with the optical fibers only on those portions thereof that are going to be woven into the cloth, the rest are not scratched nor notched.

Returning to FIG. 6, the optical bundle 34 may be given a protective plastic coating and trimmed to length. Fittings as shown in FIGS. 13 and 14 would be attached to the end of the optical bundle tail to enable the connection to a light source.

The lengths of cloth containing fiber optics are then suitable as a raw material for a variety of products. If the lengths of cloth are cut into other shapes, care must be taken to preserve the connection of all of the remaining optical fibers into the bundle. The exposed cut ends may be silvered after such cutting, otherwise light will be emitted from the cut ends in a higher intensity than the rest of the fabric.

As discussed earlier in this specification, mirrors 13, as in FIG. 1, are provided to reflect the remaining light that reaches the extreme end of the optical fiber. Such mirrors can be eliminated by weaving a rectangle of cloth as described above between long stretches of unwoven cloth would be cut apart at a point equi-distant between them leaving tails of optical fibers emerging along two opposite edges of each piece of fabric. Then, fold each piece of fabric in half so that the two edges having the optical fiber tails would be brought together. The resulting cloth is now one having a double thickness with optical fibers emerging along only one edge as before. The fibers are then gathered into a bundle as before and made into a many-stranded fiber optic light pipe. Attachments connect it to a suitable light source to make a complete specimen. This is usable only in cases where a double thickness of fabric can be accommodated.

Figure 11:
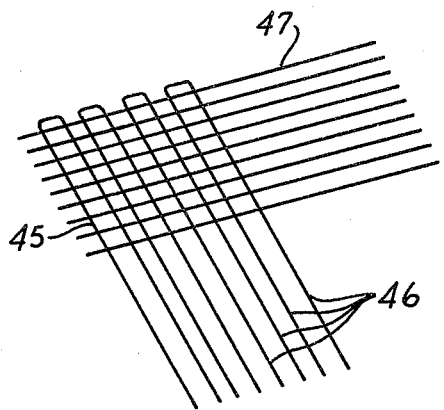
FIG. 11 shows an alternate way of weaving the fibers, with the optical fibers at one side of the fabric and having long tails at the other side of the fabric.
Figure 12:
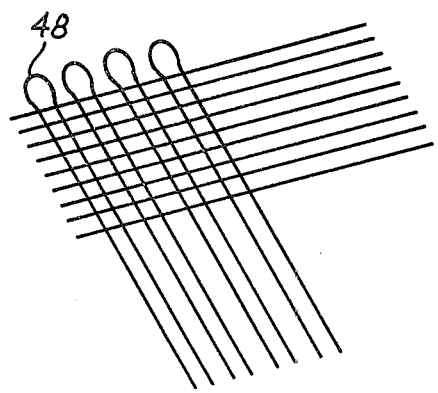
FIG. 12 shows looping of the optical fibers as shown in FIG. 11.

FIG. 11 shows an alternate method of eliminating the mirrors 13 wherein optical fibers 45 are woven as the woof on a special weaving machine that leaves long fiber optic tails 46 along one edge of the cloth and returns all optical fibers that reach the other edge 47 of the cloth. The advantage of this arrangement is that the cloth may be cut to many different lengths before the optical fiber tails are gathered together and made into light pipes. However, very flexible optical fibers must be used to prevent breakage of the fibers along the edge where they are folded back. Some alleviation of the problem results from forming a small loop 48 at the fold ends as shown in FIG. 12.

As for the scratching of optical fibers in light emitting fabrics, by using sharp tools to produce clean scratches only on one face of a sheet of light emitting fabric, most of the light escaping from these scratches will be emitted in a direction away from the surface that is scratched and little will be emitted form the back surface. In many applications, such as in room lighting, this is a significant advantage for little light is wasted in lighting spaces that are meant to be unseen. Other used make marking on the front and back desirable. The scratch pattern need not be the same on both sides of the fabric, thus permitting completely different patterns on both sides thereof. This is of particular value when word messages are scratched therein. By scratching these messages separately, they can be read from either side with neither side being a mirror image of the other.

Another way of providing light emitting fabrics with readable signs from both sides is to have a composite material consisting of layers of light emitting fibers and other transparent materials which include a reflective mirror-like surface between the layers. This insures that light emitted from one surface does not interfere with the opposite surface.

So it is seen that I have provided a light emitting fabric which is applicable in the manufacture of household curtains and draperies, used in home or office, in large curtains as in theaters, or in any other place where hanging cloth is used for decoration. The light emitting fabrics are usable in the manufacture of blankets, rugs, cushions, fabric covered furniture, fabric wall hangings, and other household items using fabrics. Outside the home, light emitting fabrics and their associated light sources can be used in automobile upholstery, flags, sails for sailboats, and other replacements for conventional fabrics.

The present invention may be embodied in other specific forms without departing from the spirit or essential attributes thereof and, accordingly, reference should be made to the appended claims, rather than to the foregoing specification as indicating the scope of the invention.

What is claimed is:

1. A light emitting fabric comprising a woven plurality of optical fibers, each of which fibers is deformed at discrete intervals along the length thereof to allow light to radiate therefrom.

2. A light emitting fabric as set forth in claim 1, including a source of illumination and a means for connecting said source of illumination to said woven plurality of optical fibers.

3. A light emitting fabric as set forth in claim 1, wherein said optical fibers comprise the warp fibers of said fabric.

4. A light emitting fabric as set forth in claim 1, wherein said optical fibers comprise the woof fibers of said fabric.

5. A light emitting fabric as set forth in claim 1, wherein said optical fibers are used as both warp and woof fibers in said fabric.

6. A light emitting fabric as set forth in claim 1, wherein the deformaties located at discrete intervals along the length of said optical fibers consist of notches cut into said fibers.

7. A light emitting fabric as set forth in claim 6, wherein the distances between successive notches along the length of each said optical fiber progressively decrease in proportion to the distances between the source of illumination and the notches to provide for uniform emission of light along the length of each said fiber.

8. A light emitting fabric as set forth in claim 6, wherein the distances between successive notches along the length of each said optical fiber vary in a predetermined manner to cause said light emitting fabric to radiate light in a predetermined visual pattern.

9. A light emitting fabric as set forth in claim 6, wherein the depth of the notches along the length of each said optical fiber is varied in a predetermined manner to cause said light emitting fabric to radiate light in a predetermined visual pattern.

10. A light emitting fabric as set forth in claim 2, wherein said connecting means connects said source of illumination to one end of each of the optical fibers comprising said woven plurality of optical fibers.

11. A light emitting fabric as set forth in claim 10, wherein all of the adjacent optical fiber ends along a first edge of said light emitting fabric extend beyond said edge and are bundled together for connection to said source of illumination.

12. A light emitting fabric as set forth in claim 11, wherein the optical fiber ends opposite the ends connected to said source of illumination are coated with a reflective substance to redirect light from the coated ends back into the optical fibers.

13. A light emitting fabric as set forth in claim 11, wherein each successive pair of optical fibers is formed from a single optical fiber element, which element is connected at both of its ends to said source of illumination and is looped at the edge of the fabric opposite said first edge to create adjacent optical fibers.

14. A light emitting fabric as set forth in claim 11, wherein said connecting means includes an optical coupler which connects said bundled optical fiber ends to said source of illumination.

15. A light emitting fabric as set forth in claim 2, wherein said connecting means includes a color filtering means which causes colored light to enter said woven plurality of optical fibers.

16. A light emitting fabric as set forth in claim 15, wherein said color filtering means is capable of varying the color of the light in said optical fibers as a function of time.

17. A light emitting fabric as set forth in claim 1, wherein the core of said optical fibers consists of a colored translucent material which causes colored light to be emitted from said fibers.

18. A light emitting fabric as set forth in claim 1, wherein said fabric is coated with a protective coating means to prevent damage thereto from the effects of weather and corrosive chemicals.

19. An article of clothing constructed from a light emitting fabric as defined in claim 1.

20. A light emitting fabric as set forth in claim 1 including a fiberglass panel of predetermined shape, said light emitting fabric being embedded within said fiberglass panel.

21. A light emitting fabric as set forth in claim 20, wherein said fiberglass panel includes a source of illumination and a means for connecting said source of illumination to said woven plurality of optical fibers.

22. Wallpaper comprised of light emitting fabric as defined in claim 1.

23. A light emitting fabric as set forth in claim 1, wherein said fabric is mounted upon a rigid backing means of predetermined shape to provide support for said fabric.

24. A light emitting fabric as set forth in claim 23, wherein said rigid backing means includes a source of illumination and a means for connecting said source of illumination to said woven plurality of optical fibers.

25. A light emitting fabric as set forth in claim 23, wherein said rigid backing means is formed from metal.

26. A light emitting fabric as set forth in claim 23, wherein said rigid backing means is formed from a cellulose substance.

27. A light emitting fabric as set forth in claim 1, wherein said fabric is mounted between two sheets of glass.

28. A light emitting fabric as set forth in claim 1, wherein said light emitting fabric is embedded within a translucent glass panel.

29. A heat emitting fabric comprising a woven plurality of optical fibers, each of which fibers is deformed at discrete intervals along the length thereof to allow infrared radiation to radiate therefrom.

30. A heat emitting fabric as set forth in claim 29, including a source of infrared radiation and a means for connecting said source of infrared radiation to said woven plurality of optical fibers.

31. A garment constructed from a heat emitting fabric as defined in claim 29, wherein all of the discrete intervals at which each said optical fiber is deformed are arranged to radiate infrared radiation toward the interior of said garment.

32. A heat emitting fabric as set forth in claim 29, wherein said heat emitting fabric is mounted upon a rigid backing means of predetermined shape to provide support for said fabric.

33. A garment woven from a plurality of optical fibers, each of which fibers is deformed at discrete intervals along the length thereof to allow ultraviolet radiation to radiate therefrom in a direction toward the interior of said garment.

34. A garment as set forth in claim 33, including a source of ultraviolet radiation and a means for connecting said source of ultraviolet radiation to said woven plurality of optical fibers.

35. A garment as set forth in claim 34, including a timing means to regulate the amount of ultraviolet radiation radiating from said optical fibers as a function of time.

* * * * *